(12) United States Patent
Pierce et al.

(10) Patent No.: US 7,578,983 B2
(45) Date of Patent: Aug. 25, 2009

(54) AUTOMATED ACCELERATED EXTRACTION OF TRACE ELEMENTS FROM BIOMASS

(75) Inventors: David T. Pierce, Grand Forks, ND (US); Wayne S. Seames, Grand Forks, ND (US)

(73) Assignee: The University of North Dakota, Grand Forks, ND (US)

( * ) Notice: Subject to any disclaimer, the term of this patent is extended or adjusted under 35 U.S.C. 154(b) by 354 days.

(21) Appl. No.: 11/471,224

(22) Filed: Jun. 20, 2006

(65) Prior Publication Data

US 2006/0283813 A1 Dec. 21, 2006

Related U.S. Application Data

(60) Provisional application No. 60/595,266, filed on Jun. 20, 2005.

(51) Int. Cl.
*C01G 23/00* (2006.01)
(52) U.S. Cl. .................. 423/75; 210/664; 210/758; 23/127
(58) Field of Classification Search .............. 423/10; 210/137, 664
See application file for complete search history.

(56) References Cited

U.S. PATENT DOCUMENTS

| 4,587,098 A | * | 5/1986 | Ohtsuka et al. ............... 422/7 |
| 4,946,797 A | | 8/1990 | Neas et al. |
| 5,147,551 A | * | 9/1992 | Averette ...................... 210/640 |
| 5,647,976 A | * | 7/1997 | Rothe et al. .................. 210/137 |

FOREIGN PATENT DOCUMENTS

| CA | EP 0485668 | * | 5/1992 |
| WO | WO 95/34360 | * | 12/1995 |

OTHER PUBLICATIONS

"Comparison of digestion methods for the determination of selenium in fish tissue by cathodic stripping voltammetry" David F. Lambert. Analytica Chimica Acta 408 (2000) 97-102.*
"High-pressure Microwave Digestion for the Determination of Arsenic, Antimony, Selenium and Mercury in Oily Wastes" Milford B. Campbell et al. Analyst. vol. 117: 121-124(1992).*
"Speciation of Selenium Compounds" by Krystyna Pyrzynska. Analytical Sciences, Jun. 1998, vol. 14. 479-483.*
"Evaluation of microwave Digestion adn solvent Extraction for the Determination of Trace Amounts of Selenium in Feeds and Plant and animal Tissues by Electrothermal Atomic absorption Spectrometry". Pierre Hocquellet et al. Analyst, vol. 116.505-509 (1991).*
Comparison of digestion methods for the dertemination of selenium in fish tissue by cathodic stripping voltammetry. By David Lamber. School of Ecology and Environment, Deakin University. Warrambool, Vic 3280, Australia. Received Jun. 8, 1999. Analytica Chimica Acta (2000). 97-102.*
Evaluation of Microwave Digestion and Solvent Extraction for the Determination of Trace Amounts of Selenium in Feeds and Plant and animal tissues by Electrothermal atomic absorption spectrometry. By Pierre Hocquellet and Marie-Paule Candillier. Analyst, May 1991, vol. 116.*
Inorganic selenium speciation using HPLC-ICP-haxaole collision/reaction cell-MS. By S Mazan, N. Gilon et al. First published as an Advance Aricle on the web Feb. 25, 2002.*
High-pressure Microwave Digestion for the Determination of Arsenic, ANitmony, Selenium and Mercury in Oily Wastes. By Milford B. Campbell and Greoge A. Kanen. Analyst, Feb. 1992, vol. 117.*
Lambert, D.F. and Turoczy, N.J. "Comparison of digestion methods for the determination of selenium in fish tissue by cathodic stripping voltammetry", *Analytica Chimica Acta*, 408 (2000) 97-102.

* cited by examiner

*Primary Examiner*—Melvin C Mayes
*Assistant Examiner*—Colette Nguyen
(74) *Attorney, Agent, or Firm*—Kinney & Lange, P.A.

(57) ABSTRACT

A method and apparatus automates and accelerates the extraction and analysis of trace elements from biomass. The method and apparatus are especially useful at key segregation points in the food chain where speed and accuracy is necessary to separate agricultural cereals that are elevated in beneficial trace element content which provides higher value to the producer.

15 Claims, 5 Drawing Sheets

AUTOMATED ACCELERATED EXTRACTION OF TRACE ELEMENTS FROM BIOMASS

BACKGROUND OF THE INVENTION

Numerous investigations have reported both positive and negative efficacy of dietary selenium in preventing or causing a variety of human conditions. Selenium is known to be an essential micronutrient for human beings; as an agent for antioxidant defense it acts as a catalyst for production of thyroid hormone and is vital for proper functioning of the human immune system. In addition, recent studies have shown that its deficiency can lead to a variety of health risks. For example, selenium deficiency is associated with increased cancer risk, occurrence of cardiovascular diseases, adverse mood states and infertility in males. In contrast, higher concentrations of selenium in human beings can be toxic. Therefore, the United States recommended dietary allowance of selenium is 55-70 ug/day for an average healthy individual.

To effectively monitor the concentrations of naturally occurring trace elements in agricultural products in the food chain, operators must be able to rapidly and efficiently perform highly sensitive analysis of trace elements in a variety of organic materials. Several laboratories have developed analytical methods to more precisely determine the amounts of trace elements present in agricultural biomass. By being able to rapidly distinguish between selenium-enriched and selenium-deficient agricultural raw materials, the operators can effectively facilitate the segregation of selenium-enriched biomass at shipping termination. For example, when a truck or train load of agricultural product arrives at the mill, the mill operators will have to decide within an hour whether the contents of the load should be assigned as a selenium-enriched raw material for premium pricing and sale. The only alternative presently available is a portable X-ray fluorescence spectroscopy method. However, this device does not provide sufficient accuracy with a detection limit and accuracy of around 10 parts per million weight. Furthermore, a major limitation of this method is that it measures only the selenium concentration in the surface layer of the material rather than its concentration in the entire sample.

In contrast, laboratory methods have higher sensitivity and accuracy but require significant processing time. These methods include spectroscopic methods such as hydride atomic absorption spectroscopy (HAAS), inductively coupled plasma atomic emission spectroscopy (ICP-AES), and graphite furnace absorption spectroscopy (GFAA). Other time consuming methods include inductively coupled plasma/mass spectroscopy and neutron activation. The major bottleneck with these analytical methods is the lengthy chemical digestion step that is needed to break down plant fibers and release selenium into a liquid or gaseous phase, where it can be easily analyzed. Digestion methods typically use concentrated nitric or perchloric acids as well as hydrogen peroxide, often with heating to high temperatures. These digestions often take several hours so that the turnaround time for a single analysis is insufficient for the current application. Furthermore, much of the digestion process is manual in nature, requiring highly skilled, trained analytical technologists. It would be highly desirable to develop a method and apparatus that has the combination of speed and accuracy necessary to perform this analysis at key segregation points in the food chain with a reduced requirement for technical skills.

SUMMARY OF THE INVENTION

The present invention is a method or apparatus for the automated accelerated extraction and analysis of trace inorganic compounds from biomass using a closed vessel containing at least one opening, where a pressure of 200 PSIA or greater is generated by carbon dioxide produced by the mixing of nitric acid and hydrogen peroxide with a biomass sample and then heating to accelerate chemical reaction. Surprisingly, the present invention is a method that utilizes carbon inherently contained in an organic sample as a desired component to accelerate the digestion and automate the process through carbon dioxide pressure produced from the biomass. Preferably, the present invention is directed to the automated extraction of trace inorganic compounds from agricultural cereal grains. More preferably, the present invention is further directed to the automated extraction of trace inorganic compounds from agricultural cereal grains that include buckwheat, wheat, and mustard.

In a first aspect of the invention, a method for the accelerated extraction of inorganic compounds residing in a biomass where a stable pressure of 200 PSIA or greater is produced upon addition of nitric acid and hydrogen peroxide and the chemical reaction enabled by heat. The vessel containing a biomass sample, nitric acid and hydrogen peroxide is sufficiently heated to enable a chemical reaction to generate pressure ranging from 200 PSIA to 2500 PSIA, and preferably, from 200 PSIA to 1500 PSIA, from the mixture in the vessel. The heat is maintained for a sufficient time, preferably 10 minutes or less, until the stable pressure is reached. The elevated pressure accelerates the degradation of the biomass, thereby reducing time for the sample preparation for analysis of trace elements derived from the biomass. Preferably, the biomass is any plant biomass and, more preferably, the biomass is an edible crop.

In a second aspect of the invention, a method and apparatus for the automated accelerated extraction of trace elements from biomass where a sample, nitric acid and hydrogen peroxide are placed in an extraction vessel having at least one opening which resides at the bottom of the vessel and a chemical reaction enabled by heat until a stable pressure is reached. Preferably, the pressure is at least 200 PSIA or greater and is monitored using a pressure detection device. The elevated pressure accelerates the digestion of the sample and provides for automated sampling through the opening in the vessel which is vented using a valve and tubing to a quantitative analytical instrument, preferably a spectrometer, to determine trace element concentration.

In a third aspect of the invention, a method and apparatus for the automated accelerated extraction of selenium from biomass where a sample, nitric acid and hydrogen peroxide are placed in an extraction vessel having at least one opening and a chemical reaction enabled by heat until a stable pressure is reached. The digested biomass is vented using a value and tubing to a second vessel where sulfamic acid and hydrochloric acid are added to reduce selenium from its +6 state to +4 state for detection. Preferably, the reaction is performed in a closed vessel where nitrogen gas is generated to pressurize the closed vessel for automated sampling and detection.

DETAILED DESCRIPTION OF INVENTION

"Accelerated" means less than 15 minutes in time duration.

"Biomass" means any part or portion of an organic material based on carbon. Examples of biomass include plant, animal, microbial or any other material derived from living material.

"Edible Crop" means a portion of a plant that can be processed into an edible foodstuff.

"Edible crop" means any plant to be harvested for food, livestock fodder, or another edible purpose.

Edible crops include, but are not limited to, cereals, oil crops, fruits, nuts and seeds, and vegetables.

Cereals include, but are not limited to, rice, maize, sweetcorn, barley, sorghums, millets, oat, rye, buckwheat, wheat, flax and the like.

Vegetables include, but are not limited to, peas, leaf vegetables, beans, root vegetables, stem vegetables, and the like.

Nuts and seeds include, but are not limited to, edible seeds, nuts and the like.

Oil crops include, but are not limited to, soybean, safflower, sunflower, sesame, canola, rapeseed, primose, poppy, camelina, olive, coconut, palm, cotton, soybean, palm, sugar beets, camelina, and the like.

"Enable" means to initiate, facilitate, cause, act or the like to begin a chemical reaction.

"Plant biomass" means any part or portion of a plant.

"PSIA" means pounds per square inch absolute, a measure of pressure referenced to a total vacuum.

"Self-venting" means a pressured sample where the pressure within the vessel facilitates the venting of the contents from the vessel without the use of any pumps.

"Stable pressure" means pressure readings that do not change with time under constant environmental conditions such as temperature.

Figure 1:
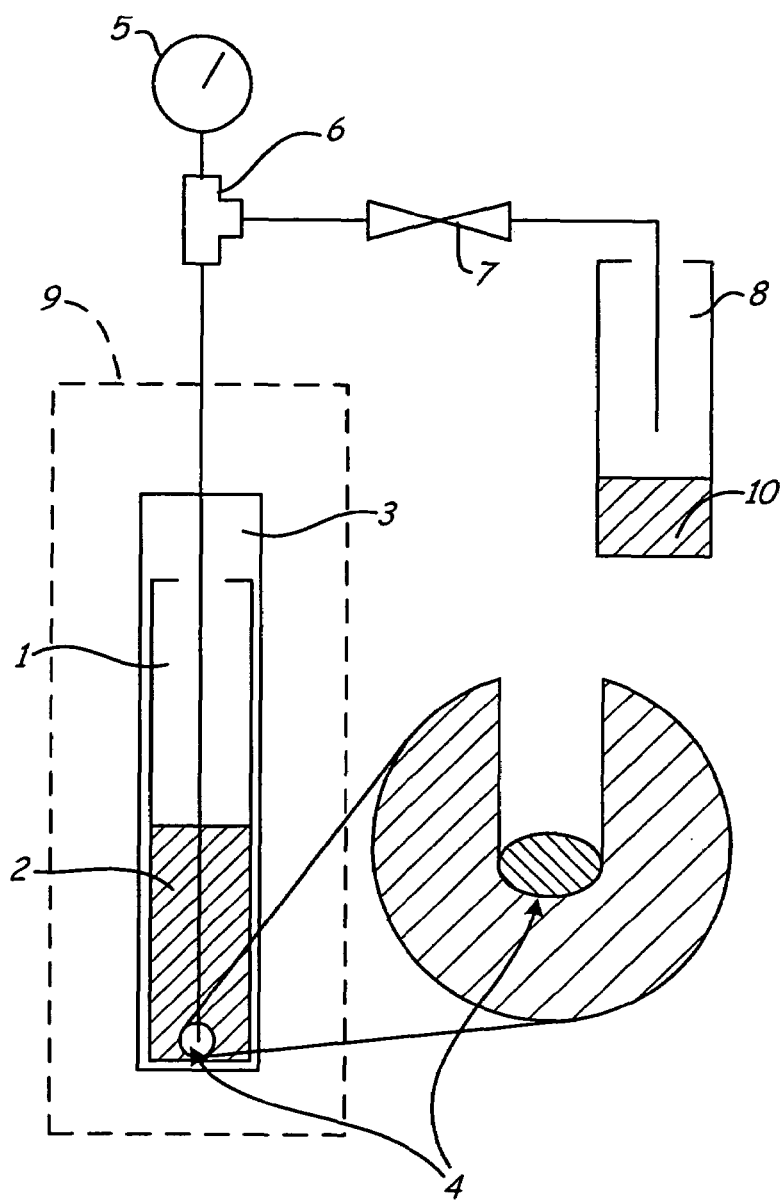
FIG. 1 is a schematic diagram of a basic apparatus for the extraction of biomass connected to an open second vessel for additional processing.

The invention described herein is for a method and apparatus for the automated extraction and analysis of trace elements from biomass. A schematic of the basic apparatus is illustrated in FIG. 1. Trace elements to be analyzed include, but are not limited to, antimony, arsenic, boron, cadmium, cobalt, chromium, copper, mercury, nickel, lead, selenium, tin, and zinc. The sample is physically degraded by any means which includes being ground, minced, diced, shredded, sliced, or the like. A sample of degraded biomass is placed in an open reaction vessel 1, and an acid mixture of nitric acid and hydrogen peroxide, (shaded area 2) is added. The sample, preferably from about 0.1 g to 2.5 g, and more preferably, about 1.0 g, is added to the acid mixture, preferably about 2 ml to 10 mL, and more preferably about 8 mL, is sufficient to generate a post-reaction pressure of about 200 PSIA to 2,500 PSIA, and more preferably about 200 PSIA to 1,500 PSIA. The open vessel 1 is then placed in a closed pressure vessel 3 able to contain about 10 mL to 50 mL, containing at least one opening 4 in the reaction vessel 1 (typical shown in inset), which is used for sampling. The reaction vessel 1 can be formed of borosilicate, aluminosilicate, alumina or quartz ceramic, and preferably, borosilicate. The exterior of the pressure vessel 3 is consistent with dimensions and metallic composition that are sufficient to withstand pressures of at least 3500 PSIA. Type 361 stainless steel is the preferred pressure vessel material, although titanium or other steels could be used. Pressure within the sealed apparatus is continuously monitored with a sensor 5 that is connected to the pressure vessel 3, for example, through tubing and a 3- or 4-port plastic union 6. The pressure sensor 5 may be monitored visually or by a computer operated device. The preferred material for the union 6 is PEEK™ and for the tubing is PEEK™ reinforced silica or like materials capable of withstanding pressures up to 3500 PSIA such as stainless steel, titanium or like materials. Sample flow through the opening 4 at the bottom of the vessel is regulated by a valve 7, that may be opened either manually or automatically using a computer operated device. The opening 4 is coupled to other vessels 8, if desired for additional reactions, or directly to a chemical analysis instrument, such as an atomic absorption spectrometer, for detection and quantitative determination of the desired trace element. Other chemical analysis instruments could be used, such as an atomic fluorescence spectrometer, an inductively-couple plasma emission spectrometer, an inductively-couple plasma/mass spectrometer, or an electrochemical analyzer.

Figure 4A:
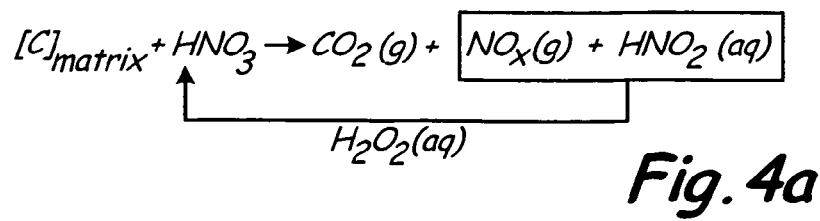
FIG. 4a is a diagram of a nitric acid and hydrogen peroxide chemical reaction.

After an appropriate amount of acid mixture is added to the reaction vessel 1 containing biomass, the reaction vessel 1 is placed in the pressure vessel 3, the pressure vessel 3 is sealed and heated to between 80° C. to 200° C., with a heat-exchanger 9 (dashed box) for a sufficient time to enable the chemical reaction. As shown in FIG. 4a, the carbon present in the sample matrix is oxidized by the nitric acid to produce $CO_2$ (g) as well as various nitrogen by-products. An unexpected improvement of the present invention as a method or an apparatus over existing methods is that carbon inherently contained in the sample, previously considered a waste product in other reported organic digestions, is used to accelerate digestion of biomass and to automate sampling. In the invention described herein, the carbon contained in the biomass is used to accelerate the digestion process in the form of carbon dioxide gas, $CO_2(g)$, produced from the chemical reaction that is used to pressurize the closed vessel to a stable level. In addition, hydrogen peroxide ($H_2O_2$) is present to oxidize hazardous $NO_x$ (g) by-products back to nitric acid under pressure, thereby driving the digestion to completion and preventing the buildup of toxic gases in the pressurized vessel headspace while producing $CO_2(g)$. After a sufficient time, preferably less than 10 minutes, more preferably less than 5 minutes and most preferably less than 2 minutes, a minimum pressure of at least 200 PSIA, is derived in part or all from $CO_2(g)$ produced from the sample matrix. The pressured sample is maintained for sufficient time to effectively accelerate the at least 80%, preferably 90%, more preferably 95% and most preferably 98% digestion of the biomass sample, which is accomplished after 10 minutes at the maintained, preferably after 5 minutes, and most preferably after 1, 2, 3 or 4 minutes pressure.

After the digestion period is complete, the pressure vessel 3 is usually cooled to about 50° C. or lower temperature, and preferably with the heat exchanger or cooling device 9. Unexpectedly, the trapped $CO_2$ (g) is used to automatically expel the aqueous sample residing in the reaction vessel by opening the valve 7 to facilitate subsequent analysis or processing. In the present invention, reaction vessels 1 that withstand a pressure of at least 200 PSIA are employed to facilitate the production of $CO_2$ (g), which is produced as a result of the chemical reaction in the form of $CO_2$ (g) from the carbon backbone in the organic sample matrix, and subsequently used to automate analysis without any additional pressurization or pumps.

Figure 2:
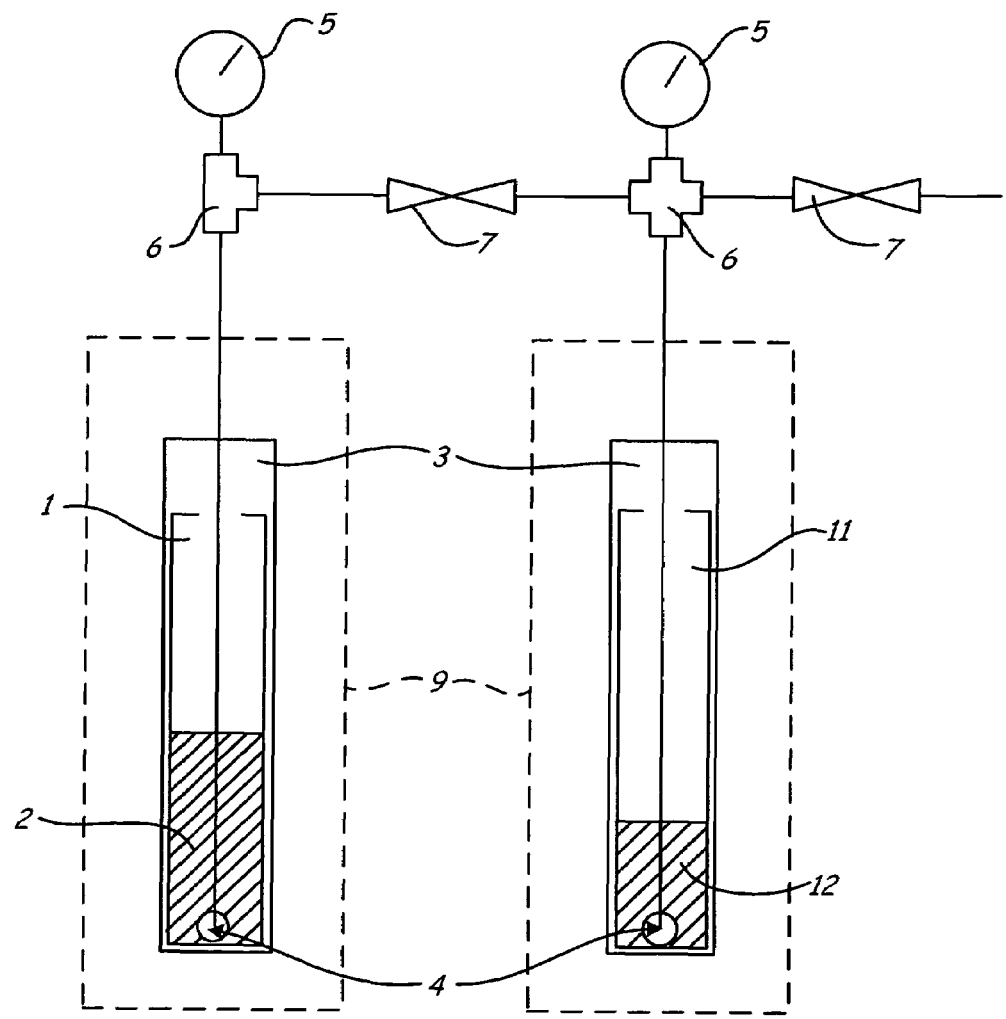
FIG. 2 is a schematic diagram of the basic apparatus connected to a closed second vessel for additional processing.
Figure 3:
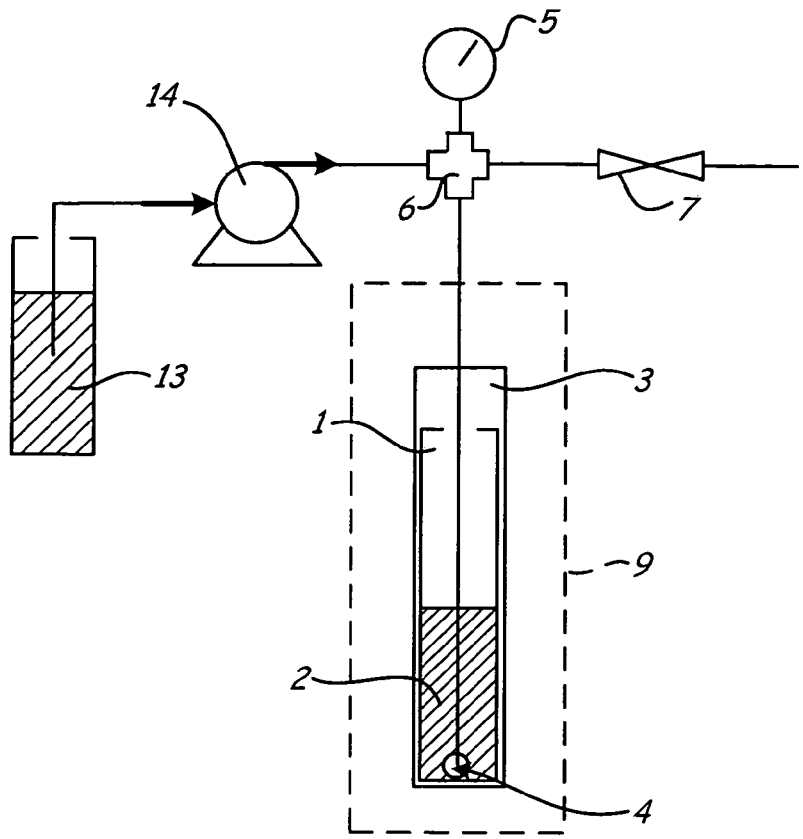
FIG. 3 is a schematic diagram of the basic apparatus where the primary vessel is used additional processing.
Figure 4B:
FIG. 4b is a diagram of a sulfamic acid and sulfuric acid chemical reaction.

If a second reaction is required for additional processing prior to analysis, the sample is released into a second vessel (vessel 8 in FIG. 1 or vessel 11 in FIG. 2). Alternatively, the pressure vessel 3 or union 6 may contain additional openings to introduce other reagents after the initial reaction is complete. The secondary reaction desired is one that creates pressure (FIG. 3). For example, for quantification of selenium concentration the digested sample can be mixed with appropriate amounts of a nitrite reductant and hydrochloric acid 10 in a separate open vessel 8 (shown in FIG. 1). More preferably, the secondary reaction 12 is performed in a separate closed vessel (in FIG. 2) or in the same pressurized vessel if the extra reagents are delivered as a solution 13 by a high-pressure metering pump 14 composed of PEEK™ or other suitable material (shown in FIG. 3). The nitrite reductant, such as sulfamic acid or urea, removes the nitrites that cause interferences (FIG. 4b) and the hydrochloric acid reduces selenium from its +6 state to +4 oxidation state. During the reaction, nitrogen gas is generated which pressurizes the closed vessel systems in FIGS. 2 and 3 and expels the aqueous sample to the analytical detection system. Similar to the first reaction vessel 1, the pressurized system is used to facilitate automated sampling. The end product is +4 state selenium in a liquid acidic medium suitable for detection by existing devices, such as hydride generation atomic absorption spectroscopy.

EXAMPLE 1

Extraction and Detection of Selenium in Cereal

Figure 5:
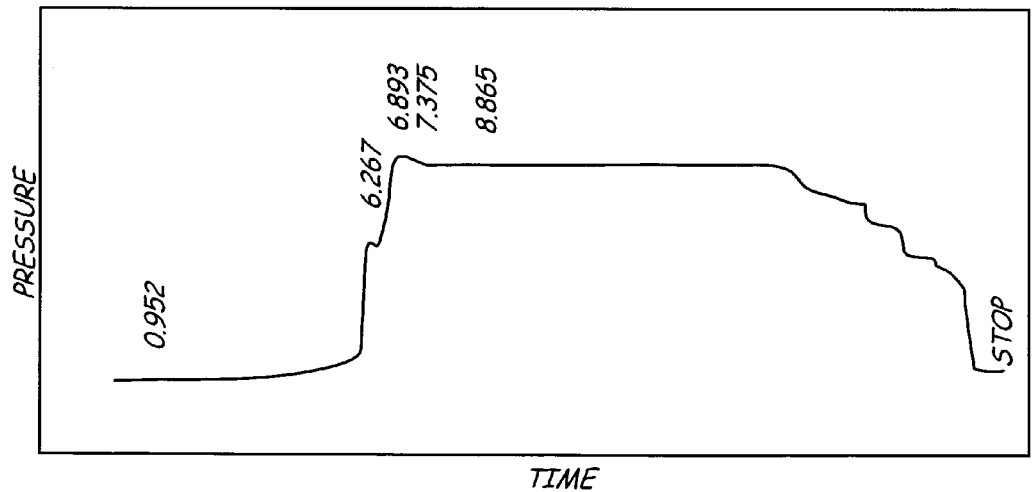
FIG. 5 is a graph showing a relationship of time and increased pressure produced by the chemical reaction caused by heating biomass, hydrogen peroxide, and nitric acid in the primary vessel.
Figure 6:
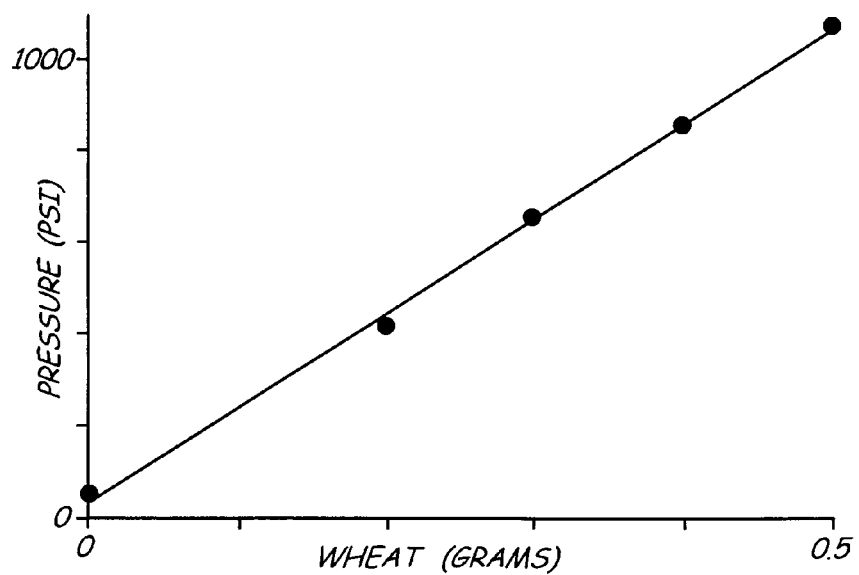
FIG. 6 is a graph showing a relationship of biomass sample size and pressure produced during chemical reaction.

An effective amount of ground buckwheat, ranging from 0.2 g to 2.5 g of coarsely ground sample was placed in a digestion system illustrated in FIG. 1. Approximately 8 ml of a 50-50 by volume mixture of nitric acid and hydrogen peroxide was added to the vessel. The biomass sample in solution was rapidly heated using a heat exchange block to a temperature of about 150° C., at which point rapid pressurization occurred within 10 minutes upon enabling the chemical reaction (FIG. 5). As a result of the reaction between the carbon-based organic matter in the sample and the acid mixture, $CO_2$ (g) was produced which rapidly increased the pressure within the vessel to least 200 PSIA or higher within 10 minutes from the initial point of heating. As shown in FIG. 6, larger samples produced more $CO_2$ (g) and increased the post-reaction pressure in direct proportion. In contrast, in the absence of a sample, pressure was limited to less than 100 PSIA. The increased pressure accelerated liquefaction of the sample, thereby facilitating the release of trace elements, such as selenium, from the organic matrix. Typically, sample liquefaction was completed in less than 5 minutes, and usually less than 2 minutes, after the high pressure is reached. In addition, hydrogen peroxide helped to regenerate nitric acid and to significantly reduce the pressurized headspace of hazardous nitrogen oxide gasses (FIG. 4a).

For selenium detection, the digested sample was cooled to below 50° C. and the remaining high-pressure $CO_2$ (g) headspace expelled the sample to a vessel by opening the valve. The expelled solution was reacted with 0.5 g to 5 g of sulfamic acid and 1 to 10 ml of 50% hydrochloric acid. The sulfamic acid reduced the nitrites that create interferences and the hydrochloric acid reduced selenium from its +6 state to +4 state. The +4 state is the only form of selenium suitable for formation of its hydride. In the present example, the hydride was automatically analyzed using an atomic absorption spectrometer equipped with a hydride generator and heated quartz atom cell. Selenium concentration was quantified based on its absorbance at a specific wavelength. In wheat samples analyzed for selenium content per weight (part per million weight), the reported selenium content (in parts-per-million by weight) showed the following results:

| SRM 1567a* Wheat Flour Mean and confidence interval are statistically equivalent to the certified values | | | | |
|---|---|---|---|---|
| Date | Conc Se (ppmt) | Sample Mass (g) | Total Elapsed Analysis Time | Stable Pressure (psi) |
| 5-17-2006-A | 1.21 | 0.510 | 26:40 | 340 |
| 5-17-2006-B | 1.11 | 0.519 | 26:52 | 320 |
| 5-17-2006-C | 0.89 | 0.497 | 26:31 | 295 |
| 5-17-2006-D | 1.16 | 0.502 | 26:42 | 325 |
| 5-17-2006-E | 0.95 | 0.493 | 26:30 | 315 |
| 5-17-2006-F | 1.37 | 0.504 | 27:31 | 340 |
| 5-18-2006-A | 1.08 | 0.495 | 26:33 | 360 |
| 5-18-2006-B | 0.88 | 0.497 | 26:46 | 310 |
| 5-18-2006-C | 0.90 | 0.492 | 26:34 | 310 |
| 5-18-2006-D | 0.97 | 0.495 | 26:37 | 350 |
| 5-18-2006-E | 1.29 | 0.491 | 26:27 | 350 |
| 5-18-2006-F | 0.94 | 0.498 | 27:15 | 310 |
| 5-18-2006-G | 0.98 | 0.493 | 26:26 | 280 |
| 5-18-2006-H | 1.15 | 0.495 | 26:57 | 275 |
| 5-22-2006-A | 0.83 | 0.524 | 26:32 | 370 |
| 5-22-2006-B | 1.32 | 0.499 | 26:34 | 330 |
| 5-22-2006-C | 1.03 | 0.492 | 26:30 | 340 |
| 5-22-2006-D | 0.90 | 0.498 | 27:02 | 320 |
| 5-22-2006-E | 1.19 | 0.503 | 26:51 | 330 |
| 5-22-2006-F | 1.24 | 0.507 | 29:15 | 280 |
| Mean | 1.07 | µg/g | | |
| Standard Dev | 0.16 | | | |
| 95% Confidence Interval (+/−value) | 0.07 | | | |

*Certified Value = 1.1 + 0.2 µg/g

OTHER EMBODIMENTS

The description of the specific embodiments of the invention is presented for the purpose of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications and publications referenced herein are hereby incorporated by reference.

Other embodiments are within the claims.

What is claimed is:

1. A method for the accelerated extraction of a trace inorganic element contained in a biomass sample, the method comprising:
   a. placing the biomass sample in a closed vessel with at least one opening in the vessel;
   b. adding a strong oxidant mixture to the biomass sample;
   c. heating the vessel to initiate a chemical reaction;
   d. allowing pressure generated from the chemical reaction to reach at least 200 PSIA;

e. maintaining the pressure until the biomass sample is degraded;

f. cooling the vessel; and g. self-venting the sample through the at least one opening in the closed vessel using the pressure generated by the chemical reaction.

2. The method of claim 1, wherein the sample is vented to a second vessel or a detection device.

3. The method of claim 2, wherein the second vessel is a closed vessel with at least one opening at the bottom of the second vessel and is used for chemical reaction to convert selenium to a +4 state the method further comprising:

a. adding a nitrite reductant and acid mixture to the sample in the second vessel;

b. allowing the chemical reaction to reduce selenium to the +4 state;

c. allowing pressure generated from the chemical reaction to reach at least 200 PSI; and d. self-venting the sample through a bottom opening of the second vessel to a detection device using the pressure.

4. The method of claim 3, wherein the nitrite reductant is sulfamic acid or urea.

5. The method of claim 3, wherein the acid is sulfuric acid or hydrochloric acid.

6. The method of claim 3, wherein at least 50% of the pressure is nitrogen gas.

7. The method of claim 1, wherein the closed vessel reaches pressures between 200 PSIA and 2500 PSIA.

8. The method of claim 1, wherein the closed vessel operates at temperatures between 80°C. and 300°C.

9. The method of claim 1, wherein the strong oxidant mixture is nitric acid and hydrogen peroxide and at least 50% of the pressure is produced by carbon dioxide gas.

10. The method of claim 1, wherein the biomass sample is about 0.1 gram to 2.5 grams.

11. The method of claim 1, wherein the trace inorganic element is selected from the group consisting of antimony, arsenic, boron, cadmium, cobalt, chromium, copper, mercury, nickel, lead, selenium, tin, and zinc.

12. The method of claim 1, wherein the pressure in Step d is reached within 10 minutes after heating.

13. The method of claim 1, wherein the pressure in Step e is maintained for 10 minutes or less.

14. The method of claim 1, wherein about 90% or greater of the biomass sample is degraded.

15. The method of claim 1, wherein the biomass is an edible crop.

* * * * *

UNITED STATES PATENT AND TRADEMARK OFFICE
CERTIFICATE OF CORRECTION

PATENT NO.       : 7,578,983 B2  
APPLICATION NO. : 11/471224  
DATED            : August 25, 2009  
INVENTOR(S)      : Pierce et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 420 days.

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,578,983 B2 | Page 1 of 1 |
| APPLICATION NO. | : 11/471224 | |
| DATED | : August 25, 2009 | |
| INVENTOR(S) | : David T. Pierce et al. | |

It is certified that error appears in the above-identified patent and that said Letters Patent is hereby corrected as shown below:

In the Specification

Col. 1, line 3, please add the following Statement of Government Interest:

STATEMENT OF GOVERNMENT INTEREST
This invention was made with government support under Grant No. 58-5450-4-346 awarded by the United States Department of Agriculture. The government has certain rights in the invention.

Signed and Sealed this
Twenty-sixth Day of November, 2013

Margaret A. Focarino
*Commissioner for Patents of the United States Patent and Trademark Office*